Figure 1:
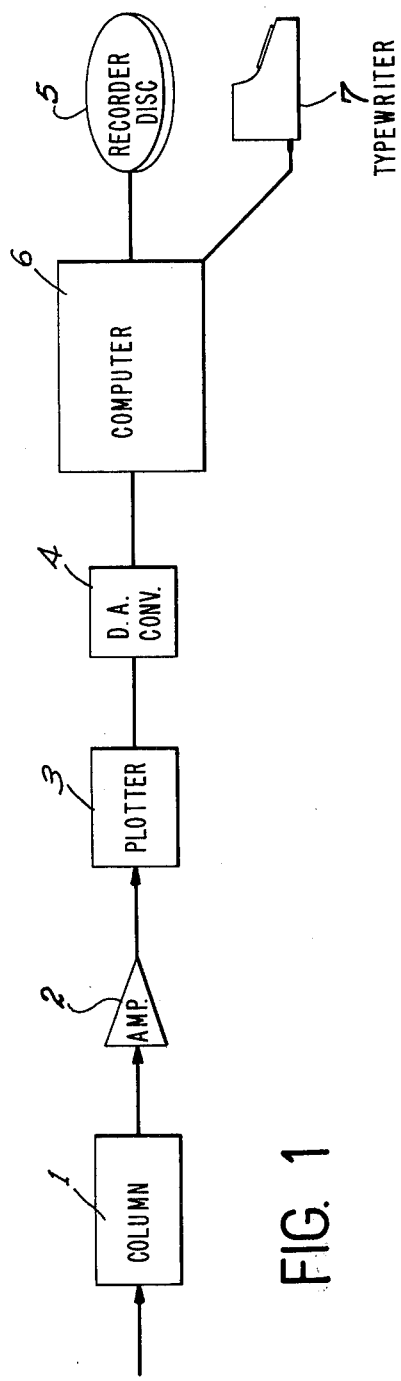

United States Patent [19]

Bordet et al.

[11] 4,002,052
[45] Jan. 11, 1977

[54] METHOD FOR THE RAPID ANALYSIS OF A MIXTURE OF A NUMBER OF SUBSTANCES BY CHROMATOGRAPHY

[75] Inventors: Jacques Bordet, Bouxieres aux Dames; Jean-Paul Gourlia, Vandoeuvre, both of France

[73] Assignee: Enterprise de Recherches et D'Activities Petrolieres Elf, Paris, France

[22] Filed: Apr. 18, 1975

[21] Appl. No.: 569,411

[30] Foreign Application Priority Data

Apr. 24, 1974 France .............................. 74.14277

[52] U.S. Cl. .................................. 73/23.1; 73/1 R
[51] Int. Cl.$^2$ ......................................... G01N 31/08
[58] Field of Search ........................... 73/1 R, 23.1; 235/151.35

[56] References Cited

UNITED STATES PATENTS

| | | | |
|---|---|---|---|
| 3,468,156 | 9/1969 | Clardy | 73/23.1 |
| 3,726,127 | 4/1973 | Putnam et al. | 73/23.1 |
| 3,863,489 | 2/1975 | Ayers et al. | 73/23.1 |

OTHER PUBLICATIONS

Lichtenstein, "Computer Automation of Chromatographic Data Processing", 1966, IEEE I.C., Record, Part 3–Computers, vol. 14.

Primary Examiner—Charles A. Ruehl
Attorney, Agent, or Firm—McNenny, Pearne, Gordon, Gail, Dickinson & Schiller

[57] ABSTRACT

In a first step, a chromatographic column is calibrated by passing separately through the column each constituent substance of the mixture to be analyzed and by recording at the exit the pulse response of said substance. In a second step, the mixture is passed through the column and the total pulse response corresponding to the mixture is recorded. In a third step, the concentration of each substance is determined from the total pulse response corresponding to the mixture and the specific pulse responses of each substance.

2 Claims, 2 Drawing Figures

METHOD FOR THE RAPID ANALYSIS OF A MIXTURE OF A NUMBER OF SUBSTANCES BY CHROMATOGRAPHY

This invention relates to a method for the rapid analysis of a mixture of a number of substances by chromatography.

It is known that chromatographic analysis is a highly efficient method for detecting and measuring the components of a complex mixture of substances. However, this method has the disadvantage of being time-consuming. For example, in order to analyze a complex mixture of hydrocarbons ranging from the paraffins to the aromatics, it is thus necessary to employ a conventional chromatographic column having a length of 3 to 10 meters and the time of analysis is at least ½ hour.

This is highly objectionable when it proves necessary for the operation of a refinery unit, for example, to obtain rapid information at each instant in order to permit automatic modification of column settings as a function of the change in composition of the mixture. The conventional chromatographic technique proves to be much too slow for this type of application and recourse must accordingly be had to mass spectrometry but this process entails the use of cumbersome equipment.

The present invention is precisely directed to a method of rapid chromatographic analysis which overcomes the disadvantages mentioned in the foregoing and makes it possible in particular to obtain extremely rapid information in regard to the composition of a mixture and to react and to modify the settings automatically as a function of these practically instantaneous data.

The method according to the invention is characterized in that, in a first step, a chromatographic column having a retention time within the range of a few seconds to 2 minutes in the case of the most strongly retained component is calibrated by passing separately through the column each of the substances used for the formation of the mixture which is to be subsequently analyzed in said column and by recording at the exit the pulse response of each substance aforesaid in respect of said column; in a second step, the mixture to be analyzed is passed through said column and the total pulse response corresponding to said mixture is recorded; in a third step, the concentration of each substance aforesaid in the mixture is calculated by a suitable mathematical method on the basis of the total pulse response corresponding to the mixture and the specific pulse responses of each substance. The retention time corresponding to the retention time of the most strongly retained component is therefore dependent on the number and nature of the substances to be separated. The minimum retention time in the case of a simple separation process can be established at approximately 5 seconds.

An advantageous feature of the method according to the invention lies in the fact that, in a first step and in the case of a given carrier gas flow velocity, each of the substances used for the formation which is to be subsequently analyzed is passed through the column, the specific pulse response of each substance aforesaid is sampled as it is being recorded and the values $h_i(t_j)$ of said response which is surface-normed are stored in memory at each sampling instant $t_j$; in the second step, the mixture to be analyzed is passed through the column, the total pulse response corresponding to said mixture is sampled as it is being recorded and the values $x(t_j)$ of said response are stored in memory at each sampling instant $t_j$; in the third step, the concentration of each substance in the mixture is calculated by using the method of least squares or in other words by minimizing the sum:

$$S = \sum_{j=1}^{m} \left[ x(t_j) - \sum_{i=1}^{n} \alpha_i h_i(t_j) \right]^2,$$

where $m$ is the number of sampled points $\alpha_i$ represents the mass or molar percentages of each of the $n$ substances $i$ in the mixture and there is then solved the system of $n$ linear equations having $n$ unknown quantities $\alpha_i$ corresponding to the equation $\delta S/\delta \alpha_i = 0$ in respect of each substance $i$ from 1 to $n$.

Figure 2:
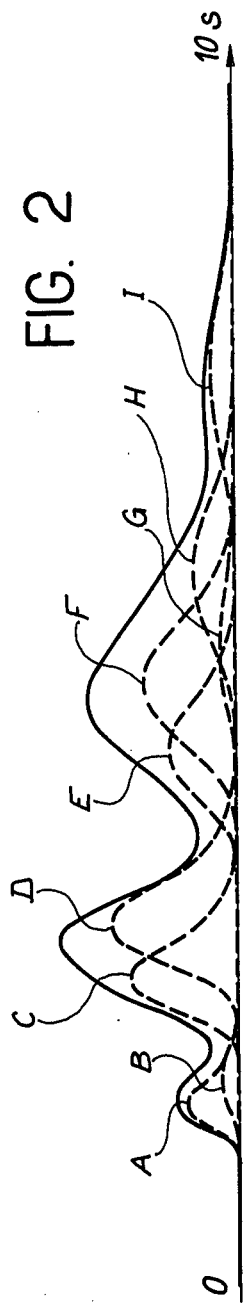

A better understanding of the invention will be obtained from the following description of one mode of execution of the method according to the invention, reference being made to the accompanying drawings wherein:

FIG. 1 is a schematic diagram of the device for carrying out the method according to the present invention; and FIG. 2 is a graph produced by the device shown in FIG. 1.

Use is made of a column having a short retention time of 2 minutes at a maximum and therefore a small length (10 to 20 cm) in respect of the usual carrier gas velocities.

Calibration of this column for each constituent of the mixture to be analyzed is carried out as follows: each substance is introduced separately into the chromatographic column 1. At the exit of the column 1, the output signal corresponding to said substance is detected and passed into an amplifier 2, then recorded in a plotter 3. At the same time, the digital-analog converter 4 samples the signal and converts the amplitude of each sample to a numerical value which it stores on a support such as a disc 5, for example.

Thus in the case of each substance $i$ of the mixture which is subsequently to be analyzed, the pulse response $h_i(t)$ is obtained and stored in memory.

In order to carry out the analysis proper, the mixture of $n$ substances $i$ whose specific signals $h_i(t)$ are known is introduced into the column 1. The total pulse response $x(t)$ corresponding to this mixture is sampled and recorded in the same manner as before.

Depending on the detector employed, the molar or mass percentages of each substance in the mixture are $\alpha_i$:

$$\sum_{i=1}^{n} \alpha = 1.$$

The total surface-normed signal obtained from the mixture is representative of the sum of signals of the $n$ components $i$ of the mixture. We therefore have:

$$x(t) = \sum_{1}^{n} \alpha_i h_i(t)$$

Since all the curves $x(t)$ and $h_i(t)$ are surfacenormed, it is necessary in order to determine the values $\alpha_i$ to minimize the sum:

$$S = \sum_{j=1}^{m} \left[ x(t_j) - \sum_{i=1}^{n} \alpha_i h_i(t_j) \right]^2$$

with respect to the values $\alpha_i$. The values $t_j$ are the sampling instants and $m$ represents the number of points of the total signal $x(t)$ sampled by the digital-analog converter 4.

In order to minimize, it is written that S is stationary with respect to the percentages $\alpha_i$, namely:

$\delta S/\delta \alpha_i = 0$ in respect of each substance $i$ from 1 to $n$, which gives $n$ linear equations having $n$ unknown quantities $\alpha_i$, which are solved numerically by setting:

$$\begin{bmatrix} H \end{bmatrix} \begin{bmatrix} \alpha_1 \\ \alpha_2 \\ \vdots \\ \alpha_n \end{bmatrix} = \begin{bmatrix} b_1 \\ b_2 \\ \vdots \\ b_n \end{bmatrix}$$

$H$ is a matrix $n.n$ corresponding to the general term:

$$h_{ij} = \sum_{k=1}^{m} h_i(t_k) h_j(t_k)$$

and $$b_i = \sum_{j=1}^{m} x(t_j) \cdot h_i(t_j)$$

It is therefore apparent that the matrix H is calculated once and for all in the case of a given group of $n$ substances $i$ and in the case of a given carrier gas velocity.

The computer 6 solves this system by means of the data contained in the computer memory and the molar or mass percentages of each of the constituents of the mixture which has thus been calculated are transmitted directly to the typewriter 7.

By adopting the method according to the invention and making use of a short chromatographic column having a short retention time, thus permitting a very rapid total pulse response which corresponds to the mixture and is too imperfect to be read directly from the graph obtained but is processed mathematically by means of a computer equipped with a digital-analog converter, a complex mixture of substances can accordingly be analyzed extremely rapidly. On the other hand, if conventional chromatography is employed in order to obtain the same result in the form of a spectrum which reproduces the signals of each component with high resolution, the length of time required would be at least ten times and in many instances up to fifty times as great.

Moreover, the method in accordance with the invention is advantageous from the point of view of quality of information; since the chromatographic analysis is performed very rapidly, this in fact circumvents the problems involved in drift of the base line which is often encountered in chromatography.

Any type of chromatographic column can be employed in the method according to the invention. However, it is necessary to ensure that the amplitude of the signal obtained in respect of the substance is proportional to the quantity of said substance introduced into the column and that the principle of superposition can be applied to the signal obtained in the case of a mixture; it is therefore preferable to operate with a low concentration and to avoid the use of a gas-solid chromatographic column.

When one of the substances assumed to be present in the mixture is not present or has disappeared, an extremely low or negative molar or mass percentage is obtained.

There is given hereunder a non-limitative example of analysis of a mixture of hydrocarbons by means of the method according to the invention.

EXAMPLE

It is sought to analyze a mixture of isopentane, N-pentane, cyclopentane, hexane, benzene, cyclohexane, cyclohexene, heptane and methylcyclohexane.

A Perkin-Elmer F-20 chromatographic column of the flame ionization type is employed. The column has a length of 15 cm, a diameter of approximately 0.3 cm and is brought to a fixed temperature within the range of 70° to 120° C. The stationary phase is constituted by squalane on "chromosorb" and the carrier gas consists of helium.

When the different constituents aforesaid have been introduced successively into the column in respect of a carrier gas velocity of 20 cm³ per minute, and when the results obtained in respect of each of these substances have been stored in memory, the mixture is introduced and the total result obtained is recorded.

The computer performs the calculation described earlier and transmits this latter to the typewriter which directly gives the molar or mass percentages of the different substances in the mixture. The following table gives these results.

| Substance | Percentage |
|---|---|
| A = Isopentane | 5 % |
| B = N-pentane | 2 % |
| C = Cyclopentane | 14 % |
| D = Hexane | 21 % |
| E = Benzene | 12 % |
| F = Cyclohexane | 21 % |
| G = Cyclohexene | 4 % |
| H = Heptane | 11 % |
| I = Methylcyclohexane | 7 % |

The degree of accuracy achieved in the results obtained is of the order of 5%.

The accompanying FIG. 2 shows the graph which is recorded by the plotter in the case of said mixture in a period of ten seconds. The full-line curve represents the graph which corresponds to the mixture. By way of a check, the curves $\alpha_1 h_1$, $\alpha_2 h_2$, $\alpha_3 h_3$ etc. which correspond to the identification signals of each constituent of the mixture have been plotted in dashed lines.

The analysis of this mixture was carried out in a time interval of approximately 30 seconds (10 seconds of analysis and 20 seconds of calculation in an IBM 1800 computer having a basic cycle of $2\mu s$). It is therefore apparent that the method according to the invention permits extremely rapid determination of the presence and concentration of components in a mixture.

The method according to the invention is applicable to any industrial method of conversion in which recourse is had to chromatographic analyses.

What we claim is:

1. A method of rapid analysis of a mixture of a predetermined number of known substances by chromatography wherein, in a first step, a chromatographic column having a retention time within the range of a few seconds to two minutes in the case of the most strongly retained substance is calibrated by passing separately through the column in the absence of each of the other substances used for the formation of the mixture which is to be subsequently analyzed in said column and by recording at the exit the pulse response of each separate substance aforesaid in respect of said column; in a second step, the mixture to be analyzed is passed through the same said column and the total pulse response corresponding to said mixture is recorded; in a third step, relating the total pulse response corresponding to the mixture and the specific pulse responses of each separate substance to determine the concentration of each separate substance aforesaid in the mixture, wherein in the first step and in the case of a given carrier gas flow velocity, the specific pulse response of each of said substances $i$ aforesaid is sampled as it is being recorded and the values $h_i(t_j)$ of said response which is surface-normed are stored in memory at each sampling instant $t_j$; in the second step, the total pulse response corresponding to said mixture is sampled as it is being recorded and the values $x(t_j)$ of said response are stored in memory at each sampling instant $t_j$; in the third step, the concentration of each of the substances in the mixture is calculated by using the method of least squares by minimizing the sum:

$$S = \sum_{j=1}^{m} \left[ x(t_j) - \sum_{i=1}^{n} \alpha_i h_i(t_j) \right]^2,$$

where $m$ is the number of points sampled and $\alpha_i$ represents the mass of molar percentages of each of the $n$ substances $i$ in the mixture and there is then solved the system of $n$ linear equations having $n$ unknown quantities $\alpha_i$ corresponding to the equation $\delta S/\delta \alpha_i = 0$ in the case of each substance $i$ from 1 to $n$.

2. A method of rapid analysis of a mixture of a number of substances this number being larger than 2 by chromatography wherein, in a first step, a chromatographic column having a retention time within the range of a few seconds to two minutes in the case of the most strongly retained component, is calibrated by passing separately through the column each of the substances used for the formation of the mixture which is to be subsequently analyzed in said column and by recording at the exit the pulse response of each substance aforesaid in respect of said column; in a second step the specific pulse response of each of said substances $i$ is sampled at times $t_j$ as it is being recorded and the values $h_i(t_j)$ of said response which is surface-normed, are stored in memory at each sampling instant $t_j$; in a third step the coefficients $h_{ij}$ of a matrix H are determined, said coefficients corresponding to the sum of the products of two values $h_i(t_k)$ and $h_j(t_k)$ for all values of sampling instant $t_k$, and then the value of the elements $h_{ij}$ of the inserted matrix H are also determined; in a fourth step the mixture to be analyzed is passed through the column, the total pulse response corresponding to said mixture is sampled as it is being recorded and the values $x(t_j)$ of said response are stored in memory at each sampling instant $t_j$; then in a first step the values of coefficients $b_i$ are determined, each coefficient being equal to the sum of products of two values $h_i(t_k)$ and $x(t_k)$ for all values of sampling instant $t_k$, and in the final step the values of the molar percentage of each of the $n$ substances $i$ in the mixture are determined by multiplying the values of $b_j$ and $h_{ij}$ for all values of $j$.

* * * * *